United States Patent [19]

Jagoe, III

[11] Patent Number: 4,522,640
[45] Date of Patent: Jun. 11, 1985

[54] MEANS FOR CHILLING CARDIOPLEGIC SOLUTIONS

[76] Inventor: A. Louis Jagoe, III, 9519 E. Stanhope Rd., Kensington, Md. 20895

[21] Appl. No.: 598,916

[22] Filed: Apr. 10, 1984

[51] Int. Cl.³ .............................................. F25D 5/00
[52] U.S. Cl. .......................................... 62/4; 128/403
[58] Field of Search ...................... 62/4; 128/402, 403; 206/219, 233

[56] References Cited

U.S. PATENT DOCUMENTS 4,000,996  1/1977  Jordan ...................................... 62/4

Primary Examiner—Frank Sever
Attorney, Agent, or Firm—Raymond N. Baker

[57] ABSTRACT

An integral, multi-compartment, disposable packaging means, made from flexible sheet material, such packaging means providing for indirect heat exchange between compartments and selective discharge of one compartment independent of a remaining compartment. A first compartment is adapted to receive and store a packaged product; walls for a second compartment are formed integrally with the first compartment establishing a sealed space for effecting indirect heat exchange between the two compartments; a reactive material capable of sustaining an endothermic or an exothermic reaction when mixed with an activating agent is held in one of such compartments. Structural means are provided enabling additives to be made independently to the two compartments and for optimum and more uniform heat transfer. In a specific embodiment, cardioplegic solution held in a first compartment is chilled sufficiently to provide a phase change in at least a portion of the solution by an endothermic reaction in a second compartment which establishes a sealed space surrounding a major portion of the first compartment. The entire packaging unit is sterilized for use in sterile environments such as operating rooms. The cardioplegic solution is discharged in a sterile condition without opening said second compartment or exposing its heat exchange media.

7 Claims, 8 Drawing Figures

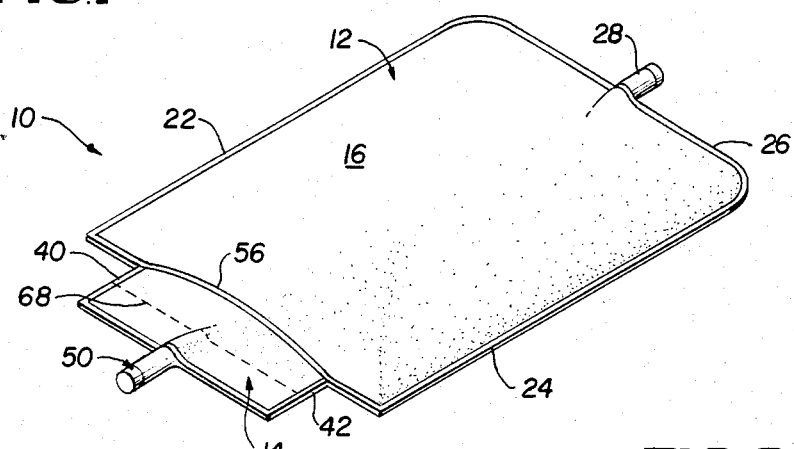
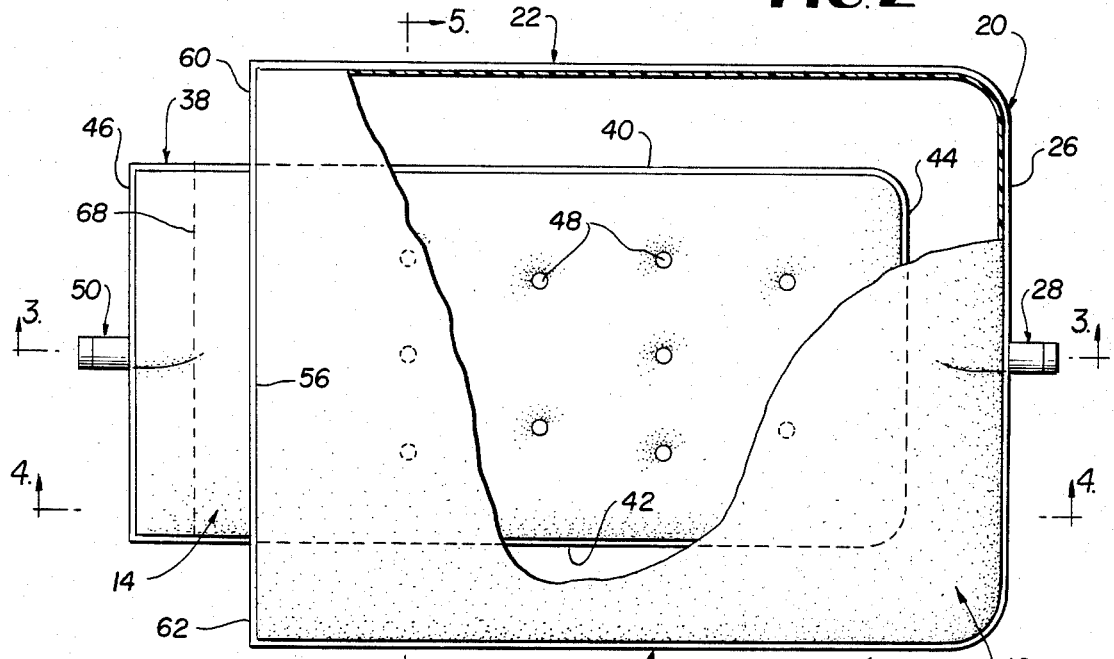
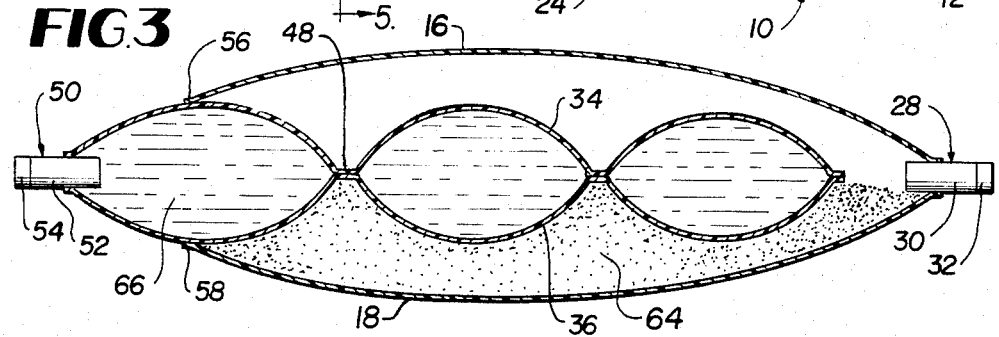

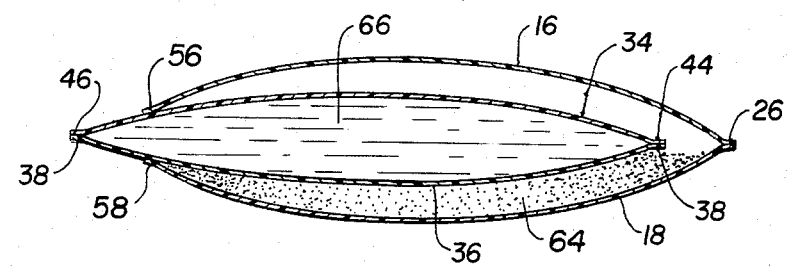
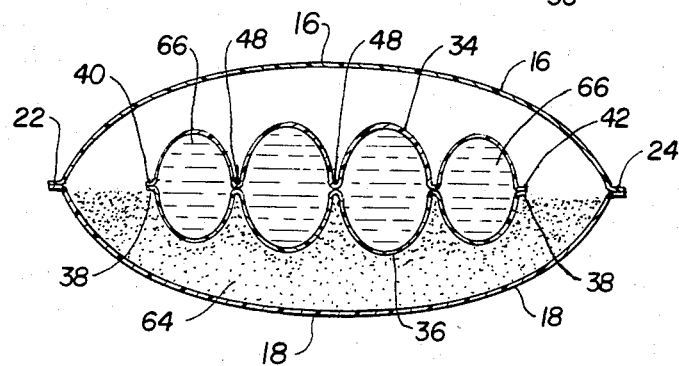
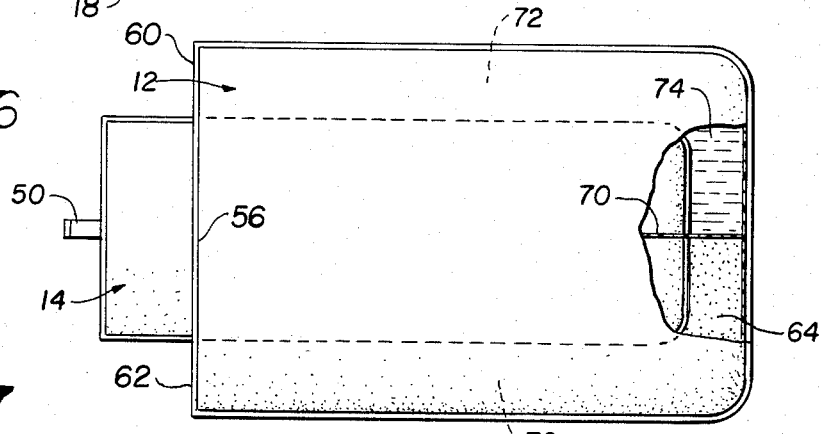
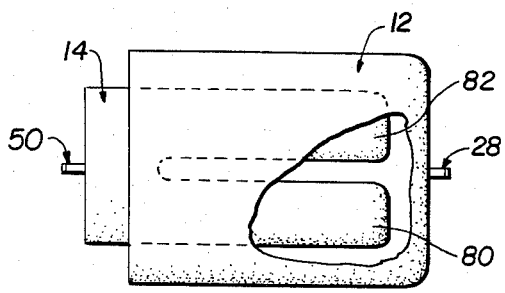
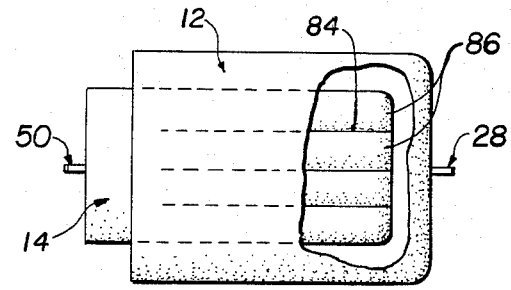

MEANS FOR CHILLING CARDIOPLEGIC SOLUTIONS

This invention relates to an integral package with individual compartments providing for indirect heat transfer therebetween and for selective discharge of a packaged product from one of such compartments. More specifically, this invention is concerned with an integral, disposable, heat-transfer package unit including a compartment for a packaged product which is either cooled or heated prior to use by indirect heat exchange from an endothermic or exothermic reaction taking place in a second compartment; and with selective discharge of such packaged product independently of said second compartment. The invention is particularly concerned with cooling sterile cardioplegic solution for use in open heart surgery.

In surgical procedures, materials in a sterile condition are often required at temperatures other than at ambient. For example, in open heart surgery, it is often necessary for the surgeon to stop the pumping action of the heart for a period of time. During the period of inaction, the heart is protected against damage by quickly chilling it to a temperature at which its metabolic rate is substantially reduced. This is accomplished by use of a chilled cardioplegic fluid which may comprise a number of constituents in a quarter-normal ($\frac{1}{4}$ normal) saline solution.

Once open heart surgery is initiated and the chest opened, chilled cardioplegic solution may be poured directly into the chest cavity around the heart where it quickly stops the heart from beating to facilitate the intricate surgical procedures and cools the heart to thereby decrease its metabolic rate and therefore its oxygen consumption, with the result that less ischemic damage is done to the heart per unit of time.

In the past, the cardioplegic solution has been chilled by, for example, a refrigerating unit as described in U.S. Pat. No. 4,249,923.

While a major constituent of cardioplegic solution is the $\frac{1}{4}$ normal saline solution, potassium salts and heparin may be used in varying amounts as is known in the art. Other pharmaceuticals may also be desired in varying amounts depending upon the patient's condition and the procedure being performed, with such materials being under the direction or control of the surgeon. It should be apparent from the above, however, that it is extremely crucial that the sterility of the cardioplegic solution is guaranteed throughout the handling, mixing and chilling procedures and until it is used in the open chest cavity. As explained in the above-mentioned U.S. Pat. No. 4,249,923, sterility of cardioplegic solutions has not always been guaranteed and the procedures for chilling have not been entirely satisfactory.

An object of the present invention is to provide an improved means for providing chilled cardioplegic solution at the point of use in a completely sterile condition.

Another object of the invention is to provide a disposable packaging means for providing such cardioplegic solution.

Another object is to provide a disposable packaging means for cardioplegic solution which includes self-contained means for chilling the cardioplegic solution to the desired degree for use in surgery.

Another object is to provide such a package for cardioplegic solution which maintains the solution in a sealed sterile condition before and after chilling and which discharges such solution independently of the heat exchange medium.

Another object of the invention is to provide such a package which will quickly chill the solution to the point of phase change converting the cardioplegic solution to a desired watery slush condition for use.

Another object of the invention is to provide such a package which may be maintained in a sterile condition so that it may be handled by operating room personnel, in the operating room environment, without contamination to such personnel or to the patient.

Another object of the invention is to provide an integral, multi-compartment heat-transfer package including a compartment for packaging a product and a compartment for providing indirect heat exchange with the packaged product and permitting selective discharge of the packaged product independently of the remaining compartment.

Another object of the invention is to provide such a package including means adapted to permit injections to be made into both compartments.

Another object is to provide such a package including a first compartment adapted to contain packaged product in a sealed sterile condition and a second compartment surrounding at least a major portion of the first compartment and containing a reactive material for generating heat transfer; the second compartment includes means for admitting an activating reagent to be added to the reactive material to initiate an endothermic or exothermic chemical reaction to cool or heat the product in the first compartment by indirect heat exchange, that is, without intermingling of the sterile product and the reactants providing for heat transfer.

Another object is to provide such a package including means enabling removal of a heated or cooled product from the first compartment while preventing the escape of the heat transfer reagent and activating agent from the second compartment.

Another object is to provide such a package including means for injecting sterile materials into the packaged product while maintaining the product compartment sealed.

In the attainment of the foregoing and other objects and advantages of the invention, an important feature resides in providing an integral package including a first compartment adapted to receive and contain a predetermined quantity of a product in a sealed sterile condition and a second compartment in contact with a major portion of the first compartment and containing a predetermined quantity of a chemical which, when contacted with an activating reagent, will sustain an endothermic or exothermic reaction for a time sufficient to indirectly heat or cool the product in the first compartment.

Preferably, the package is formed from a resilient plastic sheet material adapted to be adhesively bonded or heat sealed to close the respective compartments of the integral package and which may be readily cut to open only the first compartment to permit discharge of the sterile product for use. Preferably, each compartment also includes means to enable injections to be made into each compartment separately thus enabling additives to be injected into and mixed with a product packaged in the first compartment and an activating ingredient to be injected into the second compartment to initiate an endothermic or exothermic chemical reaction.

The package is particularly well adapted for the packaging of cardioplegic solution since the complete package may itself be packaged in a sterile condition for storage before use, and may be unpackaged in the sterile operating room environment for handling and use by sterile operating room personnel without contaminating themselves or the product. Packages of different capacity may be employed, enabling, for example, a 1,000 cc package to be used at the start of the surgical procedure, with smaller packages, for example, 250 or 500 cc packages being available to replenish the solution in the chest cavity as it warms and undergoes a phase change from the partial solid or slushy condition to a liquid; in this way, the heart can readily be maintained at a substantially uniform chilled temperature.

Other features and advantages of the invention will be apparent from the detailed description contained hereinbelow, taken in conjunction with the drawings, in which:

FIG. 1 is an isometric view of a preferred embodiment of the invention;

FIG. 2 is a plan view of the structure shown in FIG. 1, with portions broken away to more clearly illustrate the package construction;

FIG. 3 is a sectional view taken along line 3—3 of FIG. 2;

FIG. 4 is a sectional view taken along line 4—4 of FIG. 2;

FIG. 5 is a sectional view taken along line 5—5 of FIG. 2;

FIG. 6 is a view similar to FIG. 2 and showing a modification of the invention shown in FIGS. 1-5;

FIG. 7 is a plan view of an alternate embodiment of the invention; and

FIG. 8 is a plan view of a further alternate embodiment of the invention.

Referring now to the drawings in detail, an integral multi-compartment package particularly well adapted for the packaging of a product which is to be stored at ambient temperature and heated or chilled just prior to use is designated in FIGS. 1 and 2 by the reference numeral 10. The package preferably is formed from sheet material of thin gage so as to be flexible, e.g. a synthetic resin material such as polyethylene sheeting of a thickness to provide the desired strength and yet being flexible to permit ease of handling and further packaging; composite laminates of metallic foil and plastic are also representative.

Integral multi-compartment package 10 is fabricated with an external compartment 12 and an inner compartment 14 each formed from suitable flexible sheet material which can preferably be readily heat sealed or otherwise joined to itself to provide strong fluid-tight seals.

Outer compartment 12 can be formed from two flat sheets 16, 18 (FIGS. 3, 4, 5) heat sealed to one another in a continuous seam 20 extending along the side edges 22, 24 and end 26. An access valve or plug assembly 28 is integrally joined in the seam, preferably along end portion 26, to permit access to the interior of the bag 12 after completing fabrication of the package. Access assembly 28 consists of a short length of polyethylene tubing 30 positioned between sheets 16, 18 and is integrally joined thereto by the seaming operation. A plug 32 formed from a suitable resilient material such as a sterile rubber or resilient plastic material is provided in the tube 30 to form a complete fluid-tight, sterile seal. The plug 32 is adapted to be penetrated by a cannula, hypodermic needle or the like to enable injection of fluid into the bag 12 and to form a fluid-tight seal when such needle is withdrawn. Such valve plugs, per se, are known and used, for example, for the injection of medication into intravenous solutions and the like; other arrangements may be employed to provide the desired function.

The inner compartment 14 can also be made from two flat sheets 34, 36 of flexible synthetic resin material such as polyethylene sheets superimposed one on the other and joined, e.g. by heat sealing, along a seal line 38 extending around the entire periphery including opposed side edge portions 40, 42 and end edge portions 44, 46. Other configurations could be used to form the body of the respective compartments. As seen in FIGS. 2, 3 and 5, face sheets 34, 36 of inner compartment 14 are preferably joined together at a plurality of points 48 arranged in a spaced pattern to maintain the inner bag 14 in a generally flattened condition. While this may decrease the total volume of the sealed inner compartment, it will also distribute fluid within the inner compartment more uniformly thereby optimizing the ratio of surface area to volume for the indirect heat exchange taught. The sheets may be joined at points 48 by suitable means such as heat sealing or adhesive bonding in the same manner as peripheral seams 20 and 38.

An access assembly 50 is also provided for the inner compartment 14. Such assembly is preferably centrally located along end edge 46. Access assembly 50 may be identical in construction to assembly 28 and consist of a short length of a polyethylene tubing 52 with a resilient plug element 54 in the outwardly projecting end; tubing 52 is sealed in the outwardly projecting end portion of inner bag 14.

In the illustrated embodiment, outer compartment 12 is substantially wider than inner compartment 14 while the overall length of the two compartments can be substantially equal. The two compartments are assembled integrally with inner compartment 14 substantially encased by outer compartment 12 with the end at edge 44 in spaced relationship from the end at edge 26 of the outer compartment. The end near edge 46 of the inner compartment 14 is positioned to permit cutting for discharge of contents without disturbing the contents of outer compartment 12. Similarly, if outer compartment 12 is used for packaged product, the end near edge 26 of outer compartment 12 can be cut for discharge of its contents without disturbing inner compartment 14.

In the embodiment shown, the outer sheets 16, 18 are joined at edges 56, 58 to the outer surfaces of sheets 34, 36, respectively, by suitable means such as heat sealing or by adhesive, to form a fluid-tight seal. This seal continues beyond the inner compartment side edges 40, 42 along lines 60, 62 to completely seal the interior of the outer compartment 12.

In the embodiment shown, a heat transfer reactive material is placed in the outer bag 12 either prior to completing sealing the two bags 12, 14 together or it may be injected after assembly through the access assembly 28. The reactive material in sealed compartment 12 is in direct contact with the outer surface of sealed inner compartment 14. This material, illustrated at 64, can be a solid granular material before injection of an activating reagent, liquid or semi-liquid. For example, when the package is used to chill a fluid product packaged in the inner bag, ammonium nitrate may be used in solid particulate form. The endothermic chemical reaction can be initiated by injecting a predetermined volume of an activating fluid such as water into the outer bag through plug 32 of access assembly 28 by a hypodermic syringe and then shaking the package to mix the water and chemical.

Some air may be present in the sealed outer bag, but the volume of such air is preferably kept low so that the activator fluid and chemical mixture substantially fill the outer bag and completely surround the inner bag to produce more efficient heat transfer. As taught herein, the relatively large ratio of the surface area of the inner bag to its volume provided by flattening of the inner bag with weld spots 48 greatly facilitates heat exchange.

After an endothermic (or exothermic) reaction has continued for the desired time, the product 66 (FIGS. 3, 5) can be extracted through end portion 46 of the inner bag 14 while retaining the chemical and activator solution in the outer bag 12. For example, when an endothermic reaction has resulted in cooling the packaged product to the point of phase change as may be desired for cardioplegic solution, the end portion contiguous to edge 46 of the inner bag 14 can be cut along a line such as 68 which is spaced from the seal lines 56, 58; thus, only the contents of inner compartment 14 are discharged. It should be apparent also that smaller openings may be formed to permit pouring a fluid product from the inner compartment; or the product may be extracted through the assembly 50 by removal of plug 54 or use of a suitable syringe.

A modification of the structure described with reference to FIGS. 1-5 is shown in FIG. 6 wherein an internal diaphragm 70 is provided within the outer compartment 12 to form two subdivided portions. One subdivided portion 72 contains a predetermined quantity of an activating solution 74, such as water, while the other subdivided portion 76 contains a predetermined quantity of reactive material 64. Diaphragm 70 is formed from a sheet of flexible synthetic resin material and extends the full length of the outer compartment to edge seals 56, 58 on both sides of the inner compartment 14. Preferably, the same type of material as that used for plastic sheets 16 and 18 is used; but, a substantially thinner gage is provided or scorelines, or other weakened portions, for rupture are formed therein. The diaphragm 70 is joined as by heat sealing or adhesively to the external surfaces of sheets forming the inner compartment and to the internal surfaces of the sheets forming the outer compartment to provide a positive seal during storage and normal handling of the package. The thinner gage or weakened scoreline of the diaphragm 70 enables it to be ruptured by application of a force, such as by squeezing outer compartment 12, causing the activating solution 74 to flow into the compartment 76 for mixing with the reactive material to provide results as described above. In this embodiment, an access assembly 28 in the end portion of the outer bag 12 as shown in the embodiment of FIGS. 1-5 would not be necessary if only a single activator solution is to be used. For most surgical procedures, addition of an activator agent is preferred rather than relying on rupture of an internal divider membrane.

FIGS. 7 and 8 illustrate modifications of the inner bag construction which may be employed to promote rapid heat transfer between a product packaged and a mixed heat transfer solution. The construction of the heat transfer package other than the modification of the internal bag to be described is the same as described above with regard to FIGS. 1-5 and will therefore not again be described here. Also, the same reference numerals have been used to designate corresponding parts, where appropriate, throughout the drawings.

In the embodiment of FIG. 7, the inner bag 14 is divided into two tubular portions 80, 82 along a major portion of its length, with such tubular portions being in communication at at least one end. This configuration eliminates the necessity for the weld spots 48 described above while at the same time assuring a large ratio of surface area to volume of the inner bag to promote a more rapid heat transfer.

In the embodiment of FIG. 8, the initial configuration of the plastic sheets employed to form the internal bag may be identical to those employed in the embodiment of FIGS. 1-6. During production, however, the weld spots have been eliminated and replaced by a plurality of parallel seams 84 extending along a major portion of the length of internal pouch 14, thereby dividing the inner bag into a plurality of parallel, tubular portions 86 communicating at at least one end. This configuration helps assure distribution of the contents of the inner bag in such a manner as to promote rapid heat transfer.

In a specific use of the heat transfer package described, a predetermined quantity of a product such as a cardioplegic solution is packaged in the inner bag, with the product substantially completely filling the portion of the inner bag contained within the outer bag. The product may be deposited in the inner bag prior to the final seal along the end 46, or alternatively may be injected by a hypodermic-type filling device through the sealing plug 54. Since the inner bag is completely sealed, the cardioplegic solution or other product packaged remains in a sterile condition during normal handling and storage. Also, the external surface of the complete package is sterilized and packaged in a second sterile container to retain the entire package in a sterile condition. Also, the complete package can be sterilized, by radiation or otherwise, to provide sterile conditions during shipping, storage and the like so that the entire heat transfer packaging unit may be removed in a sterile operating room or other facility and remain in a sterile condition for handling by sterile personnel during a surgical procedure. When it is desired to use the packaged cardioplegic solution or other product, the activating solution is combined with the reactive material and the package shaken to thoroughly mix the activating agent and reactive material. As the chemical reaction progresses, heat transfer takes place between the walls of the compartment as described above.

By proper selection of the chemical 64 and activating solution, the desired rate of heat transfer and the degree of heating or cooling can be controlled. In the case of cardioplegic solution, it is desired that the product be quickly cooled to the point that a phase change from liquid to solid commences to take place to produce a watery slush. When this phase change has progressed to the desired extent, operating room personnel can open the package by cutting along line 68 with a suitable instrument such as a pair of scissors to permit the chilled solution to be dispensed directly from the sterile package into the chest cavity through the surgical wound. During extended surgery, it may be necessary to replenish the chilled solution in the chest cavity and this can be accomplished by activating another package at the desired time as necessary while avoiding the problems of the prior art of maintaining refrigerating apparatus in a sterile condition in the operating room and maintaining the product itself in a properly chilled, sterile condition.

While specific reference has been made to the packaging of cardioplegic solution, concepts of the present invention involving integral heat transfer packaging and selective discharge of sterile contents of a single compartment would be useful in packaging other products where it is desired to maintain a product at e.g. ambient temperature during handling and storage, and to either heat or cool the product shortly prior to use.

Other heat transfer reactive materials and activating agents than those specifically set forth are known for providing endothermic or exothermic reactions and can be used as part of the invention.

It should also be recognized that modifications may be made in configurations specifically described. For example, the outer bag may have flanges or handling tabs to enable the package to be supported from a bracket in the manner of an IV solution bag or to facilitate manual handling during opening or while dispensing the packaged product. Also, either the inner or outer compartment may be used for packaged product, with the remaining compartment for heat exchange media, to effect desired heat transfer while maintaining provision for selective discharge.

Thus, while embodiments have been specifically described for purposes of disclosing the invention, it should be understood that the invention is not so limited and it is intended to include all embodiments which would be apparent to one skilled in the art and which come within the spirit and scope of the invention.

I claim:

1. An integral multi-compartment disposable packaging unit comprising in combination means designed for transfer of heat between a thermic material and a sterile solution used in surgical procedures including a first compartment means made from flexible sheet material defining a first compartment adapted to contain a predetermined quantity of such sterile solution, a second compartment means made from flexible sheet material defining a second compartment encasing a major portion of said first compartment so as to define a sealed space therebetween providing for indirect heat exchange between said compartments, such sealed space holding a reactive material capable of providing a thermic reaction when combined with an activating reagent, and means for selectively adding an activating reagent from externally of such packaging into said sealed space for combining with and reacting with such reactive material, such reaction taking place independently of such sterile solution in said first compartment, said first compartment having a discharge portion accessible for opening and discharge of such sterile solution without discharging contents of said sealed space defined by said second compartment.

2. The packaging unit of claim 1 in which such means for selectively adding an activating reagent include means for injecting said activating reagent into said second compartment while maintaining a fluid-tight seal after such injection.

3. The packaging unit of claim 1 further including means for making an injection into said first compartment through self-sealing means which maintain a fluid-tight seal after such injection into said first compartment.

4. The packaging unit of claim 1 in which the flexible sheet material of such first compartment means defines a periphery including a peripheral end accessible for opening independently of said second compartment, with the flexible sheet material of said first compartment being joined at spaced locations within such periphery to thereby increase the ratio of surface area to volume of said first compartment so as to increase uniformity of heat transfer throughout the volume of said first compartment.

5. The packaging unit of claim 4 wherein the flexible sheet material of said second compartment is disposed to circumscribe said peripheral end of the first compartment and is joined to the external surface of said first compartment about such peripheral end to provide a fluid-tight seal between said first and second compartments.

6. The packaging unit of claim 1 in which such flexible sheet material of said first and second compartment comprises a plastic material including a synthetic resin.

7. The packaging unit of claim 1 including a sterile cardioplegic solution in said first compartment, and a reactive material in said second compartment for providing an endothermic reaction upon addition of said activating reagent such that a phase change takes place in at least a portion of such cardioplegic solution.

* * * * *